United States Patent
Peters

(10) Patent No.: US 11,305,055 B1
(45) Date of Patent: Apr. 19, 2022

(54) MEDICAL PERSONNEL SYRINGE SLOT HOLDER KIT AND TABLE TOP SYSTEM

(71) Applicant: Jenna Marie Peters, Wellington, FL (US)

(72) Inventor: Jenna Marie Peters, Wellington, FL (US)

( * ) Notice: Subject to any disclaimer, the term of this patent is extended or adjusted under 35 U.S.C. 154(b) by 0 days.

(21) Appl. No.: 17/159,623

(22) Filed: Jan. 27, 2021

(51) Int. Cl.
*A61M 5/00* (2006.01)
*A61B 50/31* (2016.01)

(52) U.S. Cl.
CPC .......... *A61M 5/008* (2013.01); *A61B 50/312* (2016.02)

(58) Field of Classification Search
CPC ....... A61B 50/312; A61M 5/00; A61M 5/008; B65D 1/24; B65D 81/18; B65D 83/10
USPC ........................................ 206/366; 211/60.1
See application file for complete search history.

(56) References Cited

U.S. PATENT DOCUMENTS

| | | | | |
|---|---|---|---|---|
| 4,836,373 A * | 6/1989 | Goldman | ............ | A61M 5/008 128/919 |
| 4,850,484 A * | 7/1989 | Denman | ............... | A61M 5/008 206/366 |
| 4,946,035 A * | 8/1990 | Grimm | ............ | A61M 37/0069 206/366 |
| 5,544,764 A * | 8/1996 | Cima | .................. | B43M 99/008 211/60.1 |
| 6,186,662 B1 * | 2/2001 | Jackson | ................... | A45C 3/00 383/117 |
| 6,637,595 B1 * | 10/2003 | Frossard | ................. | B25H 3/04 206/388 |
| 7,611,012 B2 * | 11/2009 | Ross | ..................... | A61M 5/008 206/366 |
| 7,963,396 B2 * | 6/2011 | Vanderbush | ......... | B65D 81/203 206/524.8 |
| 8,485,357 B2 * | 7/2013 | Song | .................. | B65D 21/0233 206/366 |
| 8,827,075 B2 * | 9/2014 | Seiwell | ................. | A61M 5/008 206/366 |
| 2008/0121554 A1 * | 5/2008 | Townsend | ................ | A45C 5/02 206/570 |

* cited by examiner

*Primary Examiner* — Bryon P Gehman
(74) *Attorney, Agent, or Firm* — Melvin K. Silverman

(57) ABSTRACT

Provided is a medical personnel syringe slot holder kit and table top system kit for a syringe of different lengths and widths. Also are tubes of at least two single rows of cylindrical tubes. Further, each are a corresponding of syringes of the tubes. Also provided are each of at least of each syringe with each tube, one of each row different in a diameter than of in sequence of at least of same two single rows of tubes. Further are a use of a clean plastic of a pouch of such tubes with each of the tubes with each other and vertically against each tube sufficient to permit syringes to the within kit. Also is a pouch of clear plastic of scrub pouches within a general pouch for using. The general and scrub pouches provide holding various minor nursing essential including at least bandages, alcohol wipes, betadine, gauze, and tapes.

18 Claims, 15 Drawing Sheets

Exhibit B

MEDICAL PERSONNEL SYRINGE SLOT HOLDER KIT AND TABLE TOP SYSTEM

BACKGROUND OF THE INVENTION

The present invention is a carrying case and tabletop system for the use of a plurality of syringe forms surrounded by tubes and including an attached kit with a group of packets designed to hold minor nursing essentials, to be used by medical personnel, as set forth below.

Carrying cases for syringes, outfits, and the like have appeared in prior art. An example of such is U.S. Pat. No. 1,980,141 (1934) issued to MacGregor encompassing a Cushion Carrying Case for Syringe Outfits and the like. The carrying case's primary invention is that of the components of the elements of the syringes themselves. Therein, the length of each syringe is substantially uniform or exactly the same. See also U.S. Pat. No. 3,203,302 (1965) issued to Hobbs encompassing a tamper-proof container for hypodermic syringes, where the length of each syringe is identical to each other.

U.S. Pat. No. 3,331,499 (1967) issued to Jost encompasses an improvement of the system of Hobbs.

U.S. Pat. No. 4,142,633 (1979) issued to Rayhavachari encompasses a system of identical syringes each with the other, defining a similar distance between each syringe.

U.S. Pat. No. 5,522,503 (1996) issued to Halpich encompasses a system, containing the plurality of like syringes, of determining the opening or closing of the barrel of each syringe.

U.S. Pat. No. 6,540,072 (2003) issued to Fischer encompasses a vertical and horizontal rack of syringes, all of which are the same size and diameter.

U.S. Pat. No. 9,027,721 (2015) issued to Osborne encompasses a Nurse's Travel Bag which resembles a suitcase with uniform compartments that contain a plurality of nurse-related items. The system is a travel sized bag; it includes much larger amounts of medical supplies than in Applicant's kit. It operates as a rolling case, providing a large medical supply travel system, unlike the small and limited medical supply kit of Applicant.

U.S. Pat. No. 9,572,922 (2017) issued to Leonard encompasses a System for Tools, Kits and Supplies for Use and Mobility by Diabetics. It is a pocket-sized carrying kits for usage of diabetic medications within a 24 hour period. See FIG. 1. The kit's pocket involves an apparatus with a vial for various types of syringes. See FIG. 14. It provides storage for a multiplicity of syringe forms, yet lacks the practicality of the medical supply kit of Applicant.

SUMMARY OF THE INVENTION

Included herewith is a medical personnel syringe holder kit and table top system. The system and kit provides for a plurality of syringes of different lengths, widths, diameters, and sizes. Included are at least two single rows of a plurality of cylindrical tubes. Additionally, it includes a set of corresponding syringes for each cylindrical tube. Each syringe correlates to each tube, wherein each tube in each row has a different in diameter and size than that of the next, in a sequence of at least two single rows of tubes. Also, it uses a clean plastic pouch for containing such tubes with each tube vertically against each other tube, sufficient to permit the syringes to rest within each tube within said system and kit.

It is an object of the invention to develop multiple systems because pocket sizes vary.

It is another object of the invention to provide cylindrical tubes ranging from 1 ml to 1000 mL and capable of holding 50 mL to 1 mL syringes and needles varying in diameter, with a minimum holding capacity of at least three syringes in various sizes.

It is yet a further object of the invention to provide for a system that can stand upright on a table.

Further, it is an object of the invention to provide a system of plastic that may help prevent needles from sticking medical professional if a needle cap were to come off inside the system.

In some embodiments of the invention, the tubes may be placed staggered and plastic should cover three-fourths of the syringe with a standard 5 mm (1.5 inch) needle attached.

It is additionally an object of the invention to provide cylindrical tubes 1-2 cm wider than the syringes to hold the syringes without a wrapper.

It yet further an object of the invention to provide an embodiment of the system that may have single rows of tubes with pouches (or scrub-pouches) and or double rows of tubes with no pouches.

It is an object of the invention to provide a system that can hold syringes with or without needles.

It is an object of the invention to provide a system that can hold syringes with or without medication inside.

It is an object of the invention to provide a system that is made of clear plastic and fits in scrub pockets.

It is an object of the invention to provide a system, wherein sizes vary as pocket sizes vary, but within the general length of about 100 mm for the entire kit, however, the table top system may be larger.

It is an object of the invention to provide a tubing material hard enough to prevent needle sticks, provided that the syringes are capped with a needle.

It is an object of the invention to provide a system, wherein the syringes must slide in and out of the cylindrical tubes easily.

It is an object of the invention to provide a system should easily slide out of pockets and scrub pockets.

It is yet another objective of current invention to provide a tabletop and packet system that may vary in size and/or design.

These and other objects, features, and advantages of the invention will be apparent within the description and claims, as set forth herein.

DETAILED DESCRIPTION OF THE INVENTION

As may be appreciated from the disclosure herein, multiple systems must be developed because pocket sizes vary. Cylinder tubes range from 1 ml to 1000 mL and hold 50 mL to 1 mL syringes and needles varying in diameter, with a minimum holding capacity of at least three syringes in various sizes. The system can stand upright on a table. The system of plastic may help prevent needles from sticking medical professional if a needle cap were to come off inside the system. The tubes may be placed staggered and plastic should cover ¾ three-fourths of the syringe with a standard 5 mm (1.5 inch) needle attached. In one embodiment, cylinder tubes will be 1-2 cm wider than the syringes to hold the syringes without a wrapper. In one embodiment, the system may have single rows of tubes with pouches (or scrub-pouches) and or double rows of tubes with no pouches. The system can hold syringes with or without needles. The system can hold syringes with or without medication inside. The system is made of clear plastic and fits in scrub pockets. The system sizes vary as pocket sizes, but within the general length of about 100 mm for the entire kit; the table top system may be larger. The system comprises a tubing material hard enough to prevent needle sticks, provided that syringes are secured capped with a needle. The syringes must slide in and out of the cylindrical tubes easily. The system should easily slide out of pockets and scrub pockets. The system is not considered sterile in any regard. Tabletop and packet systems may vary in size and/or design. Medical professionals must adhere to standard of care according to clinical practice guidelines.

Figure 1:
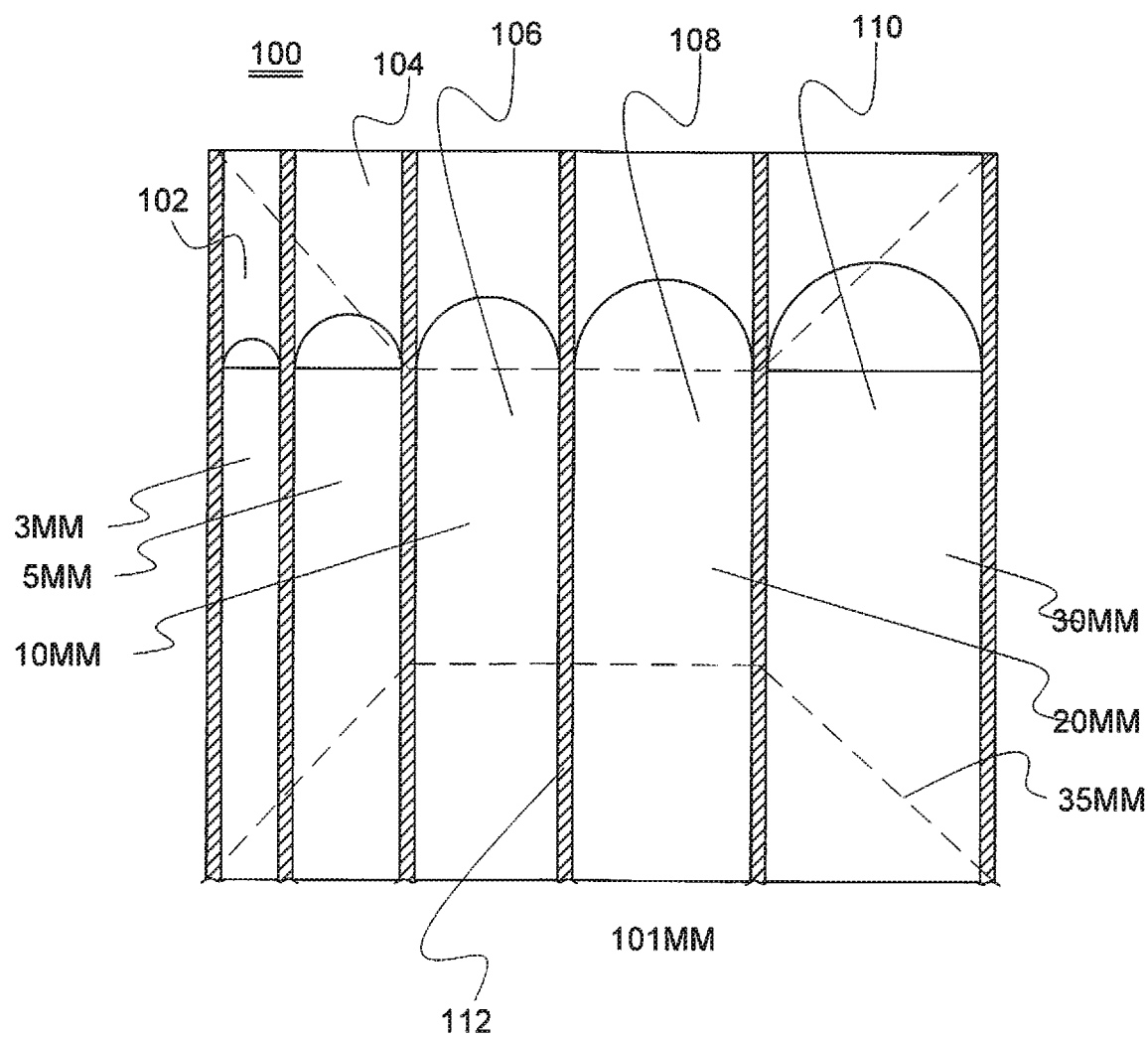
FIG. 1 is a cross-section view of the syringe-holding tubes of the system.

As is understood within the prior art above, there exists a variety of kits, cases, and systems for the use of epidermic syringes or the like, each of which have the same primary object, that of a multiplicity of syringes within the same package, rack, or container. In most prior art cases, every syringe is identical to each other. Some, such as U.S. Pat. No. 9,572,922 issued to Leonard above, encompass a kit for diabetic use; it includes a kit for a variety of functions related to the use of tools needed for an improved diabetic lifestyle. Also, it mentions that two different forms of syringes may be used. Here, the system and kit developed by the Applicant is substantially different. Whereas diabetic and other specific purpose cases or kits existed, the present system or kit provides a general purpose for the use of a packet-sized system 100 as shown in FIG. 1, intended only for use by a licensed medical professional. The system is configured to be operable within a limited space of proximately of a length of 101 mm, as shown in the schematic view of FIG. 1.

Figure 1A:
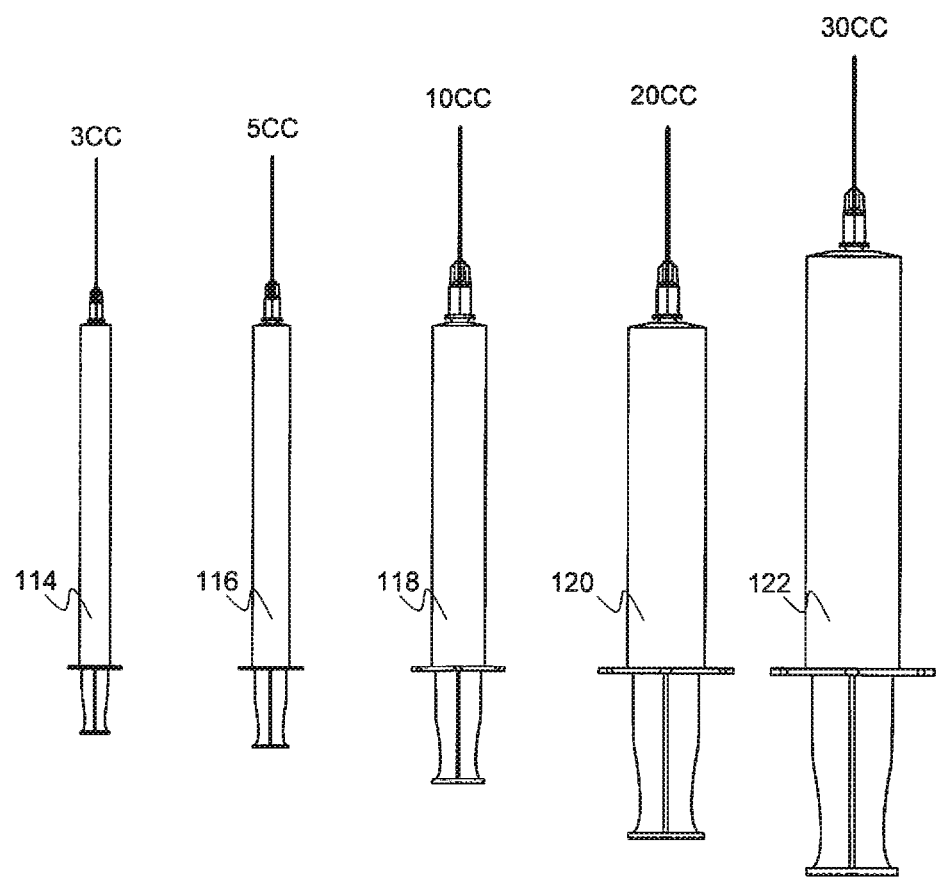
FIG. 1A shows the syringes of the system.

More specifically, the figures show the maximum capacity, or carrying capacity, with the combination of syringe sizes. Within the packet pouch system, are syringes pouch tubes with diameters of 3 mm 102, 5 mm 104, 10 mm 106, 20 mm 108, and 30 mm 110. The distance between syringes is about 1 mm, see elements 112. Also shown are needles with volumes of 3 cc 114, 5 cc 116, 10 cc 118, 20cc 120 and 30 cc 122. These aspects may be seen in FIGS. 1 and 1A.

Figure 2:
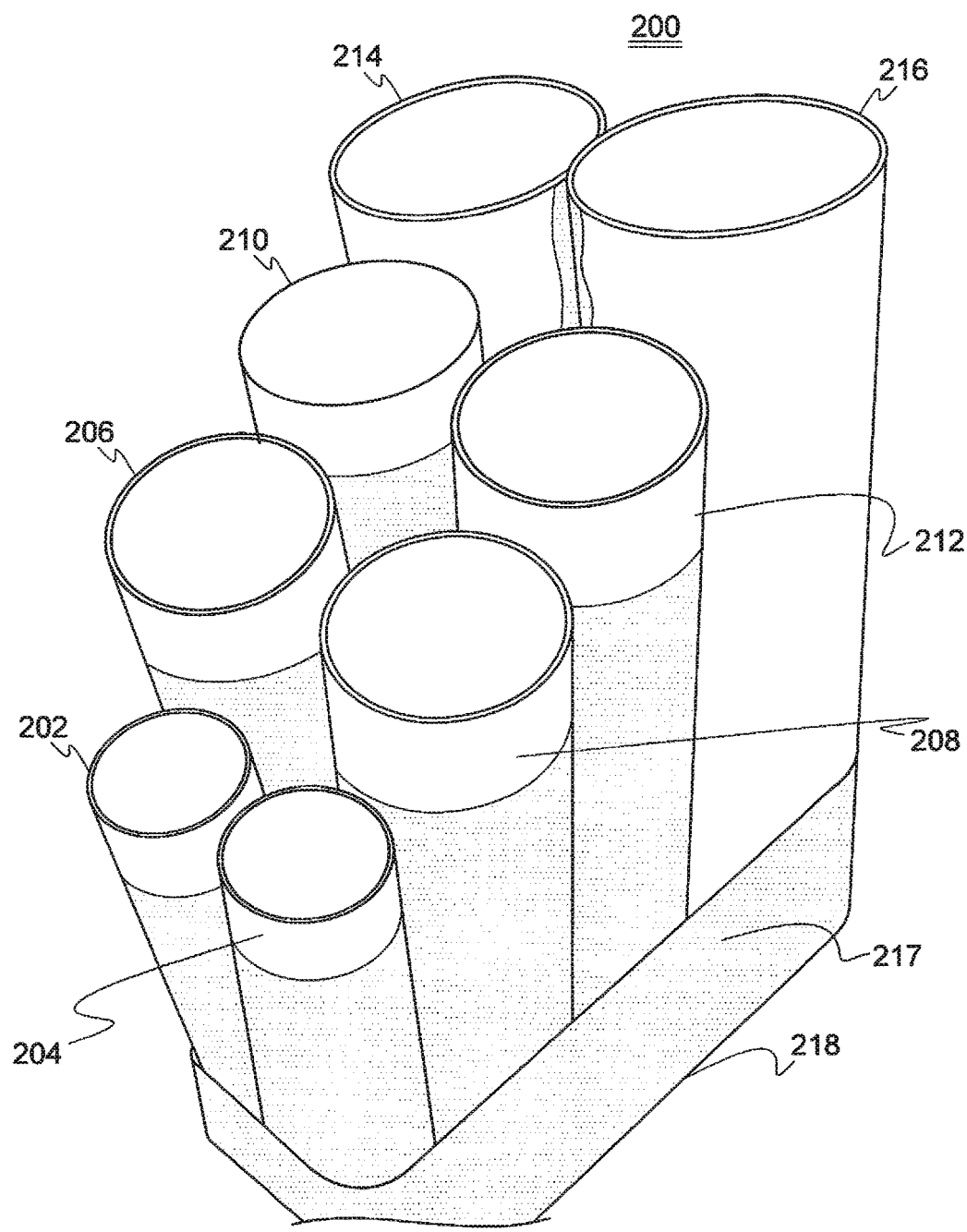
FIG. 2 shows generic tubes in a 2×4 arrangement.

Set forth in FIG. 2 are a plurality of tubes, in which each is of a different height. The tubes 200 are arranged in a 2 by 6 arrangement, as may appreciated in FIG. 2 showing tubes 202, 204, 206, 208, 210, 212, 214, and 216. Also, the tubes are surrounded by a flexible, clear plastic strip 217. All tubes 200 may connect to a flat surface 218.

Figure 3:
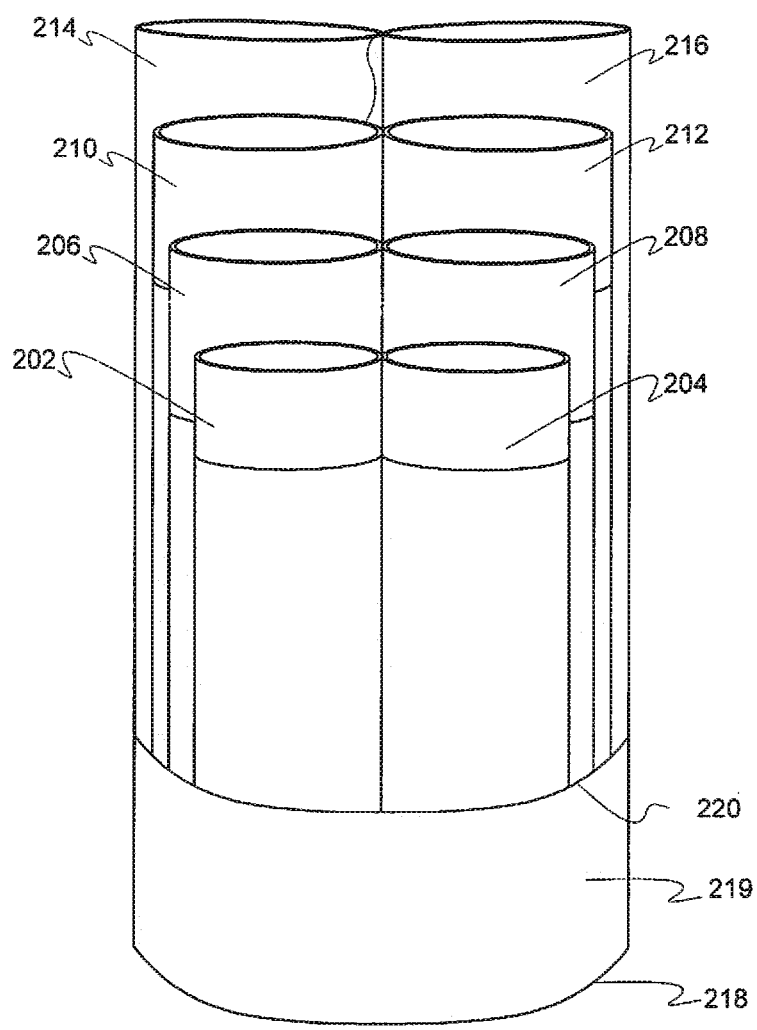
FIG. 3 is a front view of the embodiment as shown in of FIG. 2.
Figure 4:
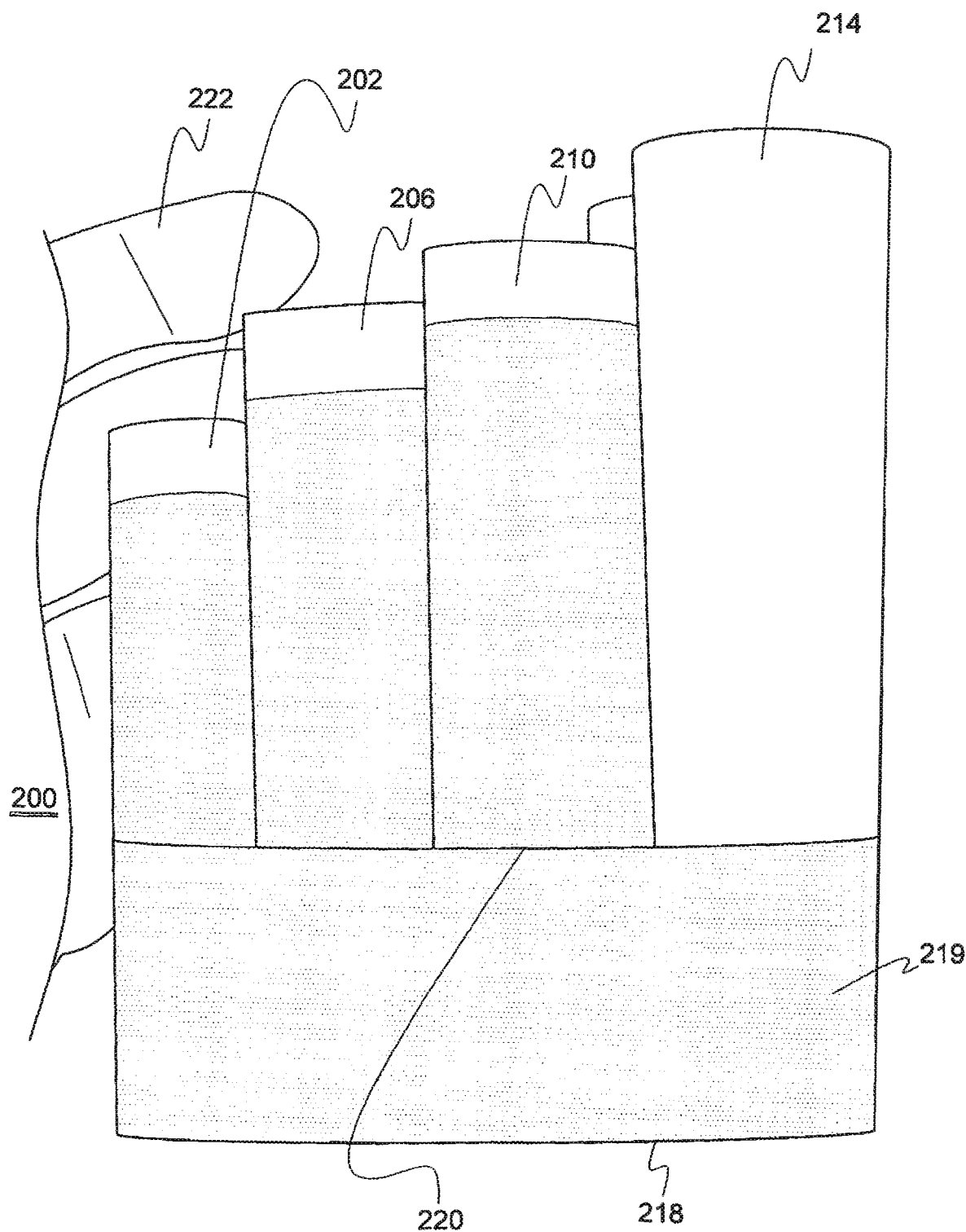
FIG. 4 is a side perspective view of the embodiment shown in FIGS. 2 and 3.
Figure 5:
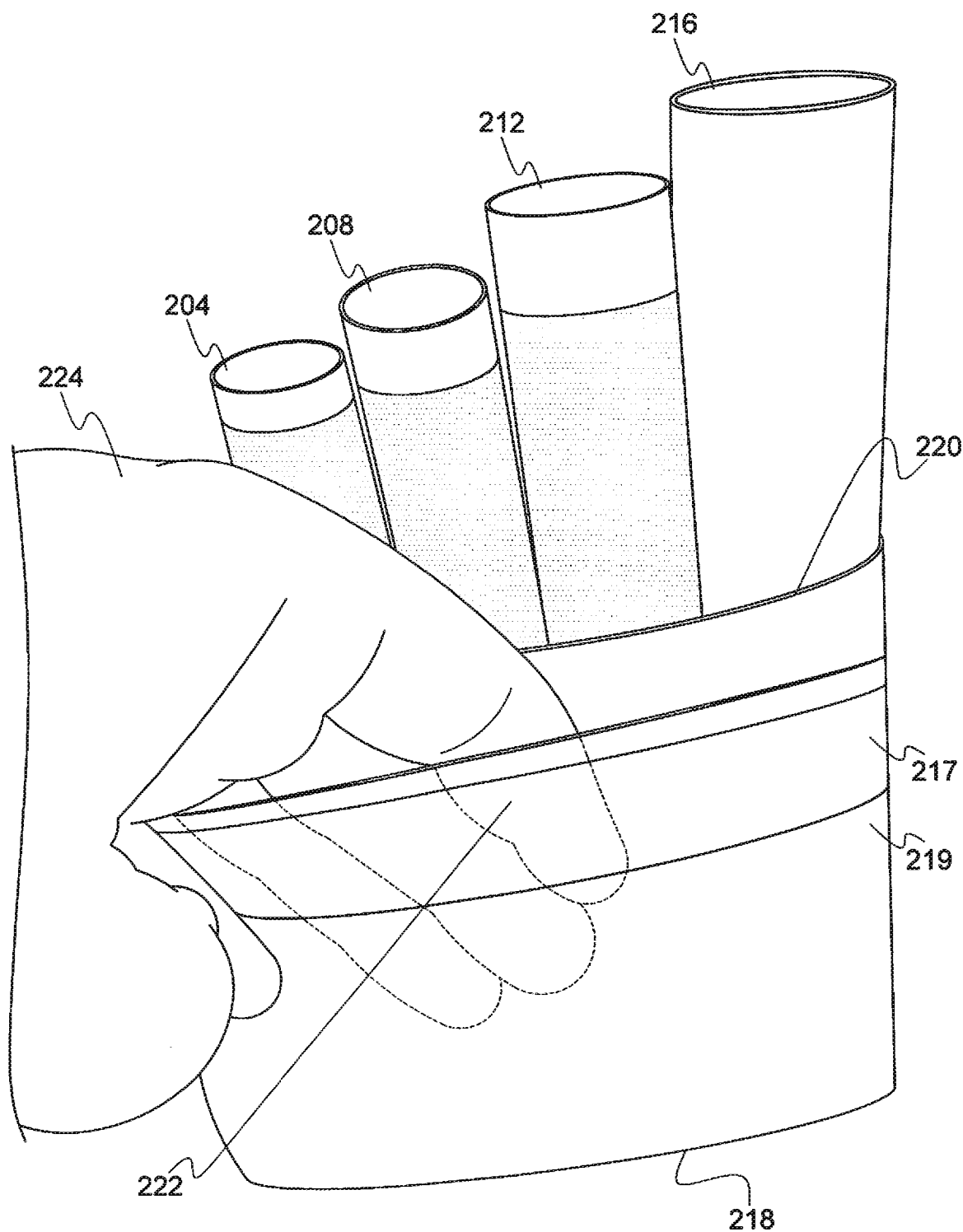
FIG. 5 is a perspective view of the system with a single row of 4 tubes, engaged in pouches.

Shown in FIG. 3 is an end view of the embodiment shown in FIG. 2. FIGS. 4 and 5 show the use of a group of said tubes 200. Each tube is surrounded by a plastic shroud 219 which also includes a lower plastic circumferential surface 220. A separable space between plastic circumferential surface 220 and plastic shroud 219 is shown in FIG. 5, as shown by the illustration of a finger 222 of a hand 224. The purpose of the figure is to show the placement of single rows of tubes 204, 208, 212, and 216. Also shown in FIG. 5 is the use of single row design that is different from the double row design of FIGS. 2 to 4.

Figure 6:
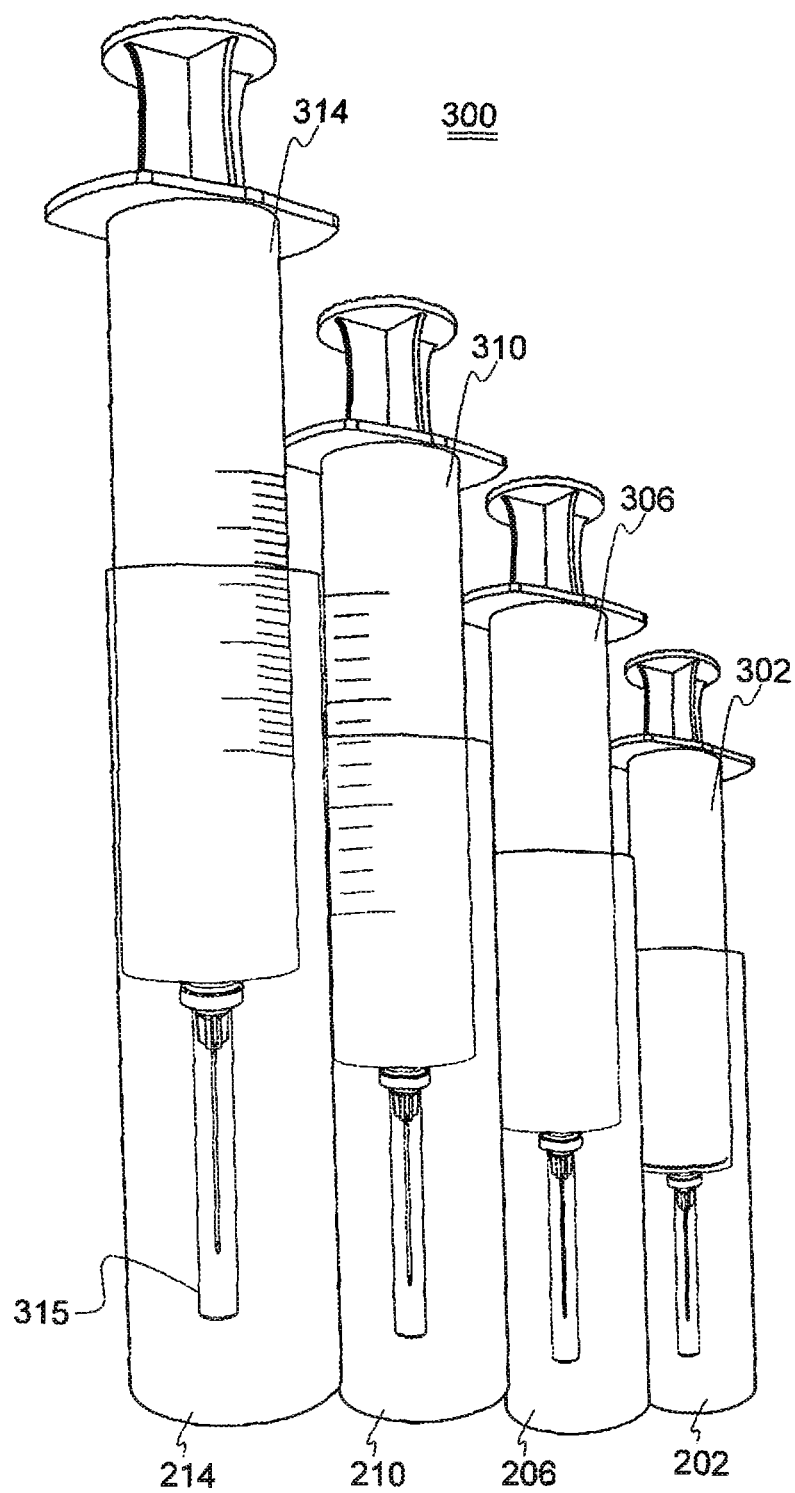
FIG. 6 shows a rear perspective of the tubes engaged with syringes.

In FIG. 6 is shown a sequence of different forms of four syringes 300, comprising syringes 302, 306, 310, and 314; each syringe correspondingly within tubes 202, 206, 210, and 214, similar to that of FIG. 5. Also included are needle caps 315.

Figure 7:
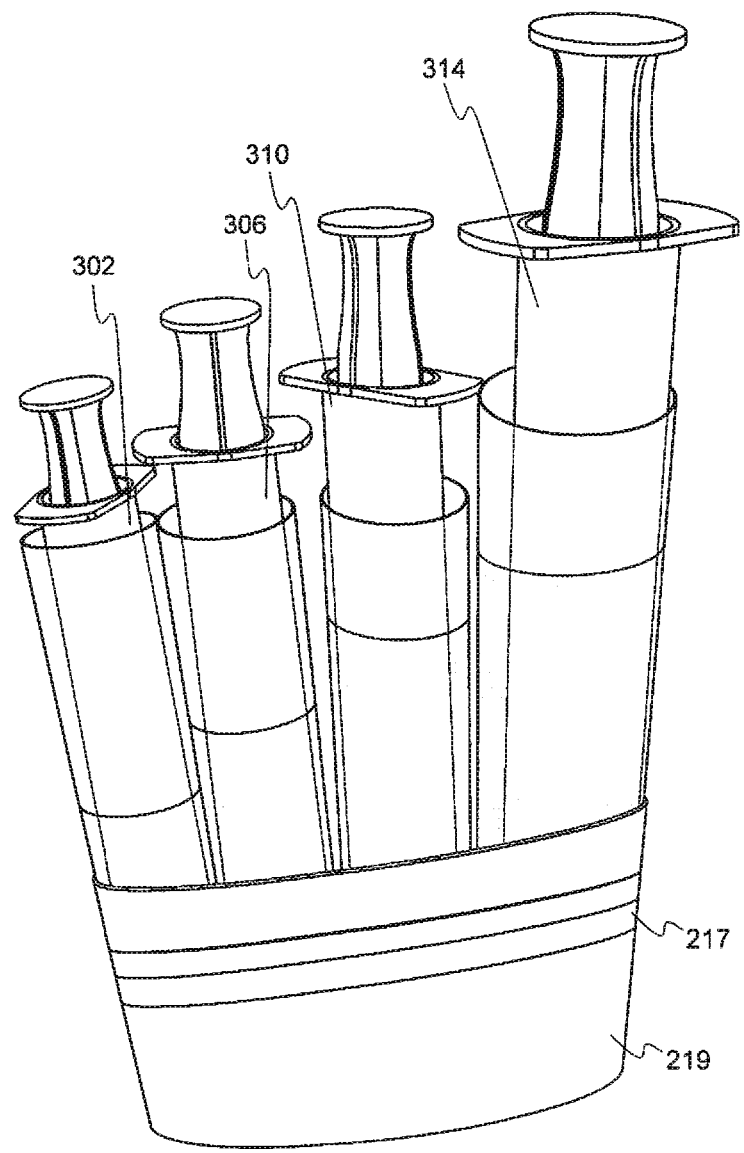
FIG. 7 shows a perspective view of a 1×4 configuration of the system.
Figure 8:
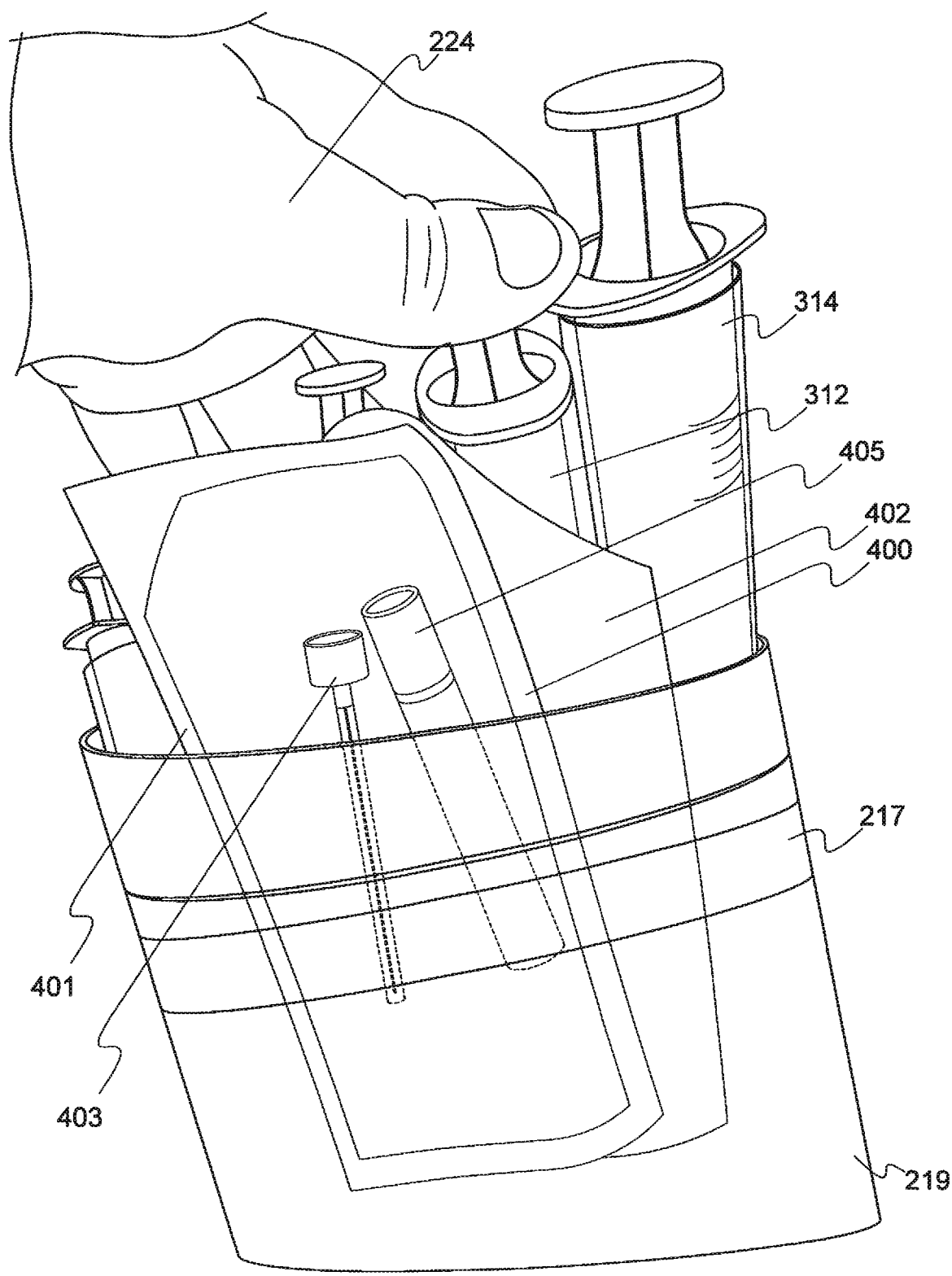
FIG. 8 is a perspective view of the system, with other medical essentials.

In FIG. 7 is shown four syringes of the type shown in FIG. 6 within the tubes, separated from each other by about 1 mm of space. Also shown in FIG. 7 is the shroud 219 of the clear flexible plastic material. Also in FIG. 7 is the same circumferential clear plastic strip 217 of the embodiment shown in FIG. 5.

Figure 9:
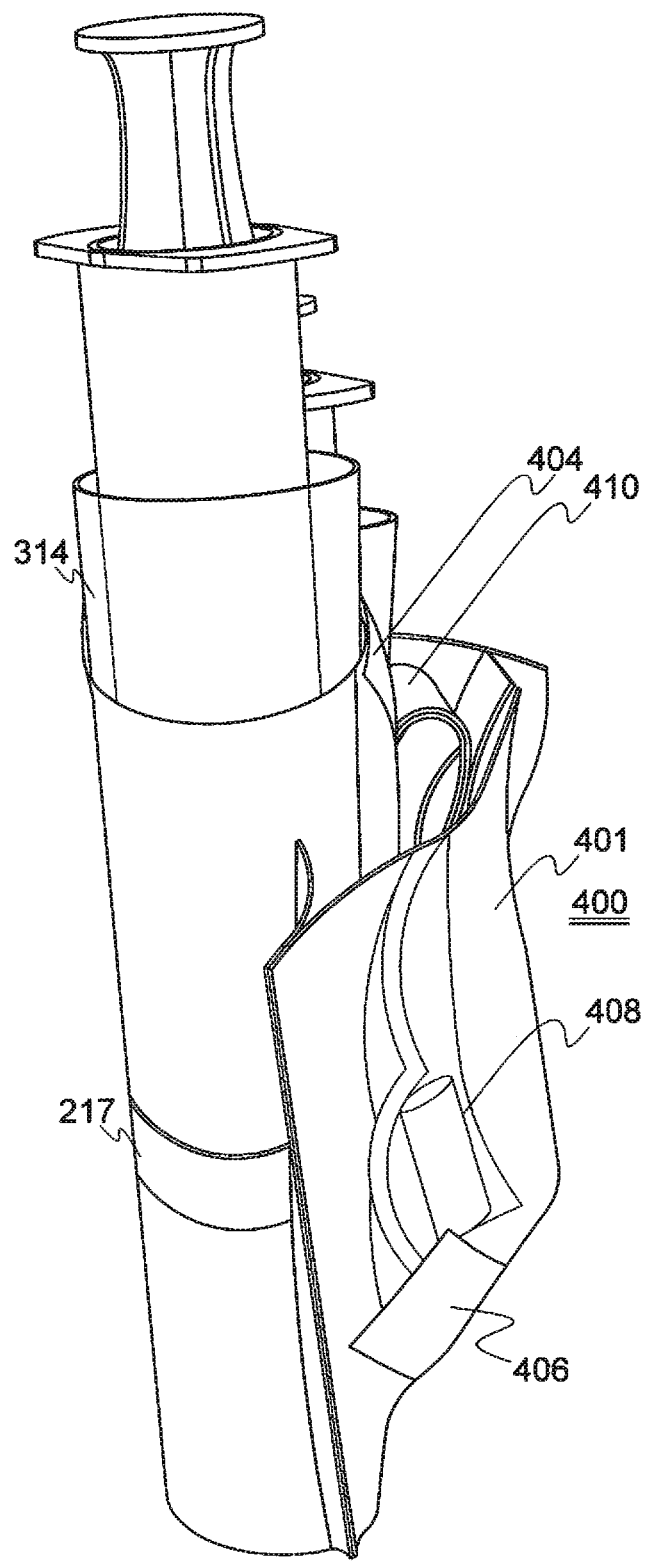
FIG. 9 is a rear perspective view of the embodiment as shown in FIG. 8.

FIGS. 8-14 show the location of a package contents of the nursing pouch essentials 400 which includes bandages 402, alcohol wipes 404, Betadine 406, gauze 408, and tape 410, among others. FIG. 9 is an edge view of that of FIG. 8, also showing that there is an arm strap 410. Elements 403 and 405 are shown as an IV start kit and PVP ampules tubing, respectively.

Figure 10:
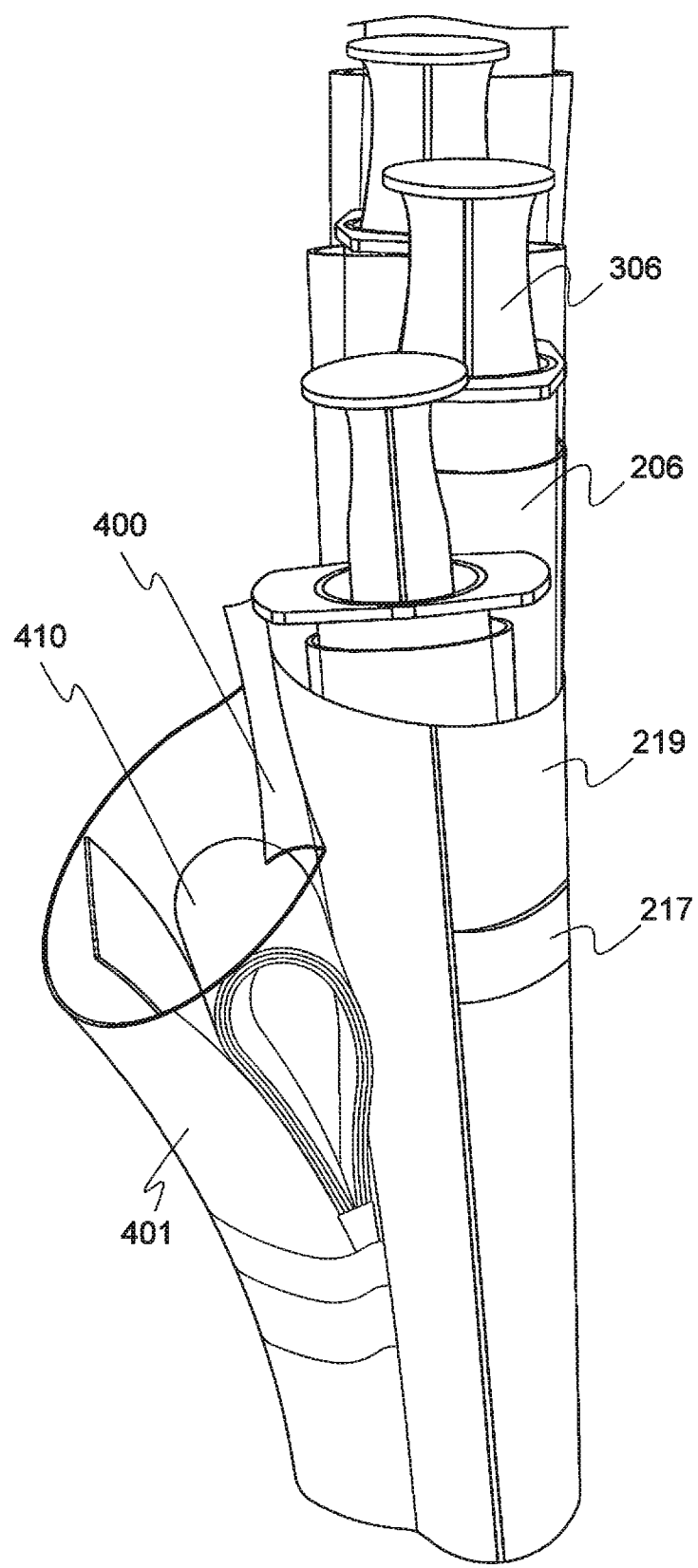
FIG. 10 is a front perspective view of the embodiment shown in FIG. 9.
Figure 11:
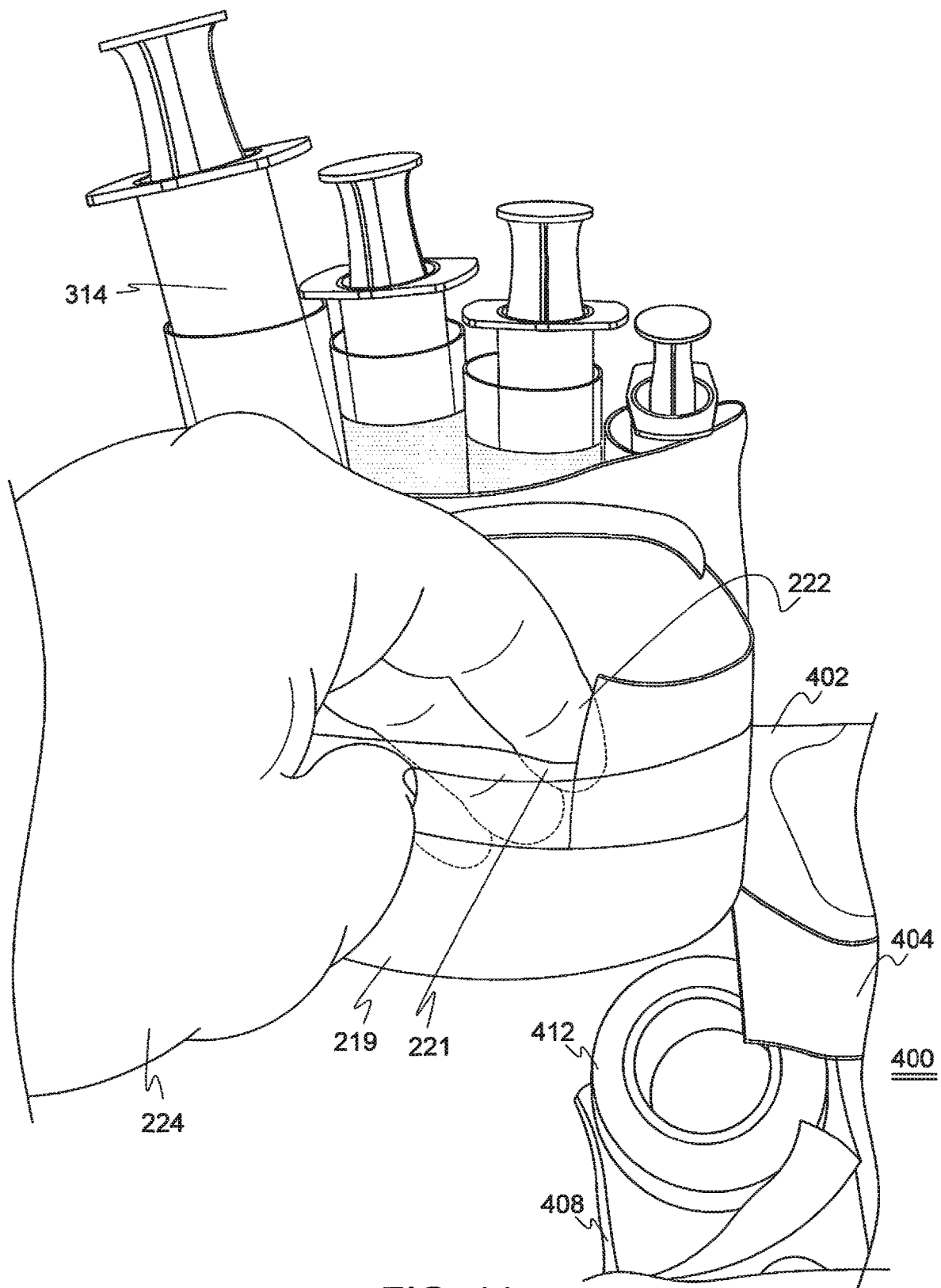
FIG. 11 is a side perspective view of the system with a user's fingers engaging therewith.
Figure 12:
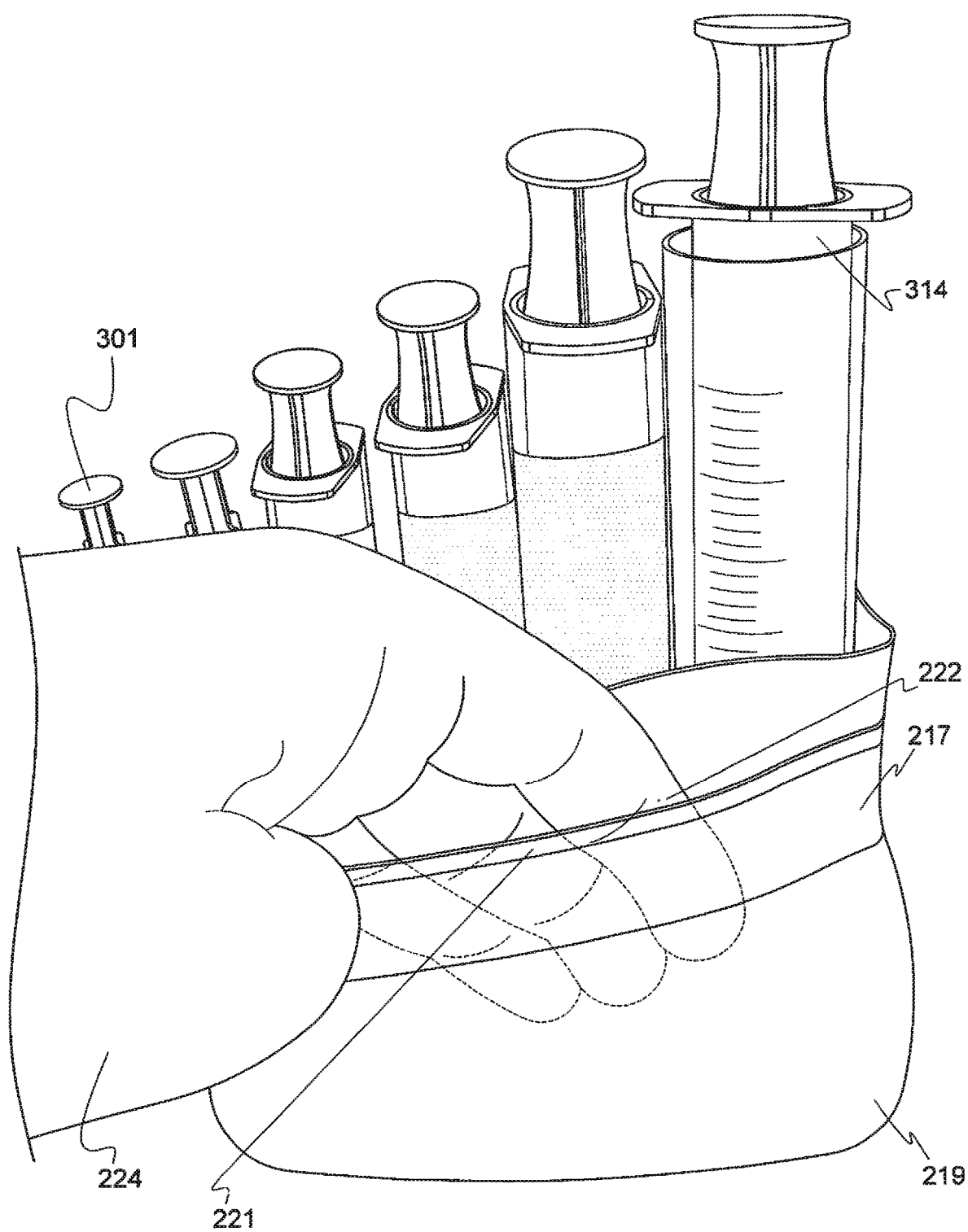
FIG. 12 illustrates a side perspective view including the use of pouches.

FIGS. 10-12 show in the use of different single types of syringes, wherein the plastic pouches 217 and 219 can be configured to be of different heights. Pouch 400 also includes scrub pouches 401.

In FIG. 11, it is also noted that the pouch essentials 400 may open at the top using an "easy" access opening or slit 221. The slit may incorporate the use of a pin, Velcro, an attachment, or a magnetic closure (not shown) on the pouch to prevent the nursing essentials from falling out in situations of tipping or lack of balance of elements within the system. Further, the bottom of the system should be slightly weighted.

FIG. 12 shows plastic pouches 217 and 219 within the pockets 221 that may be used with scrub pockets (not shown). The figure also shows that the syringes 301 will all fit within the pockets 219.

Figure 13:
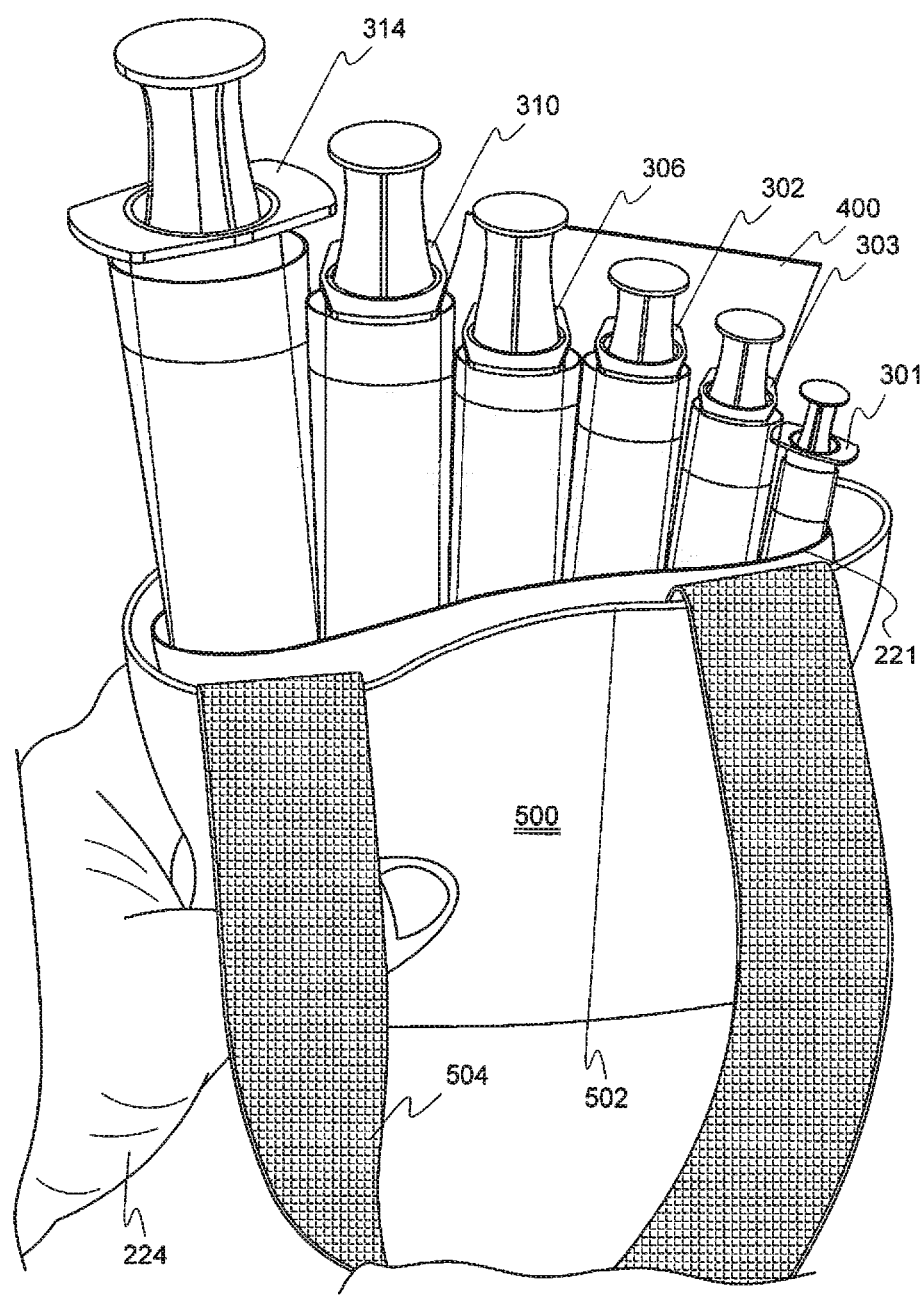
FIG. 13 is a side perspective view of the system within a handbag.
Figure 14:
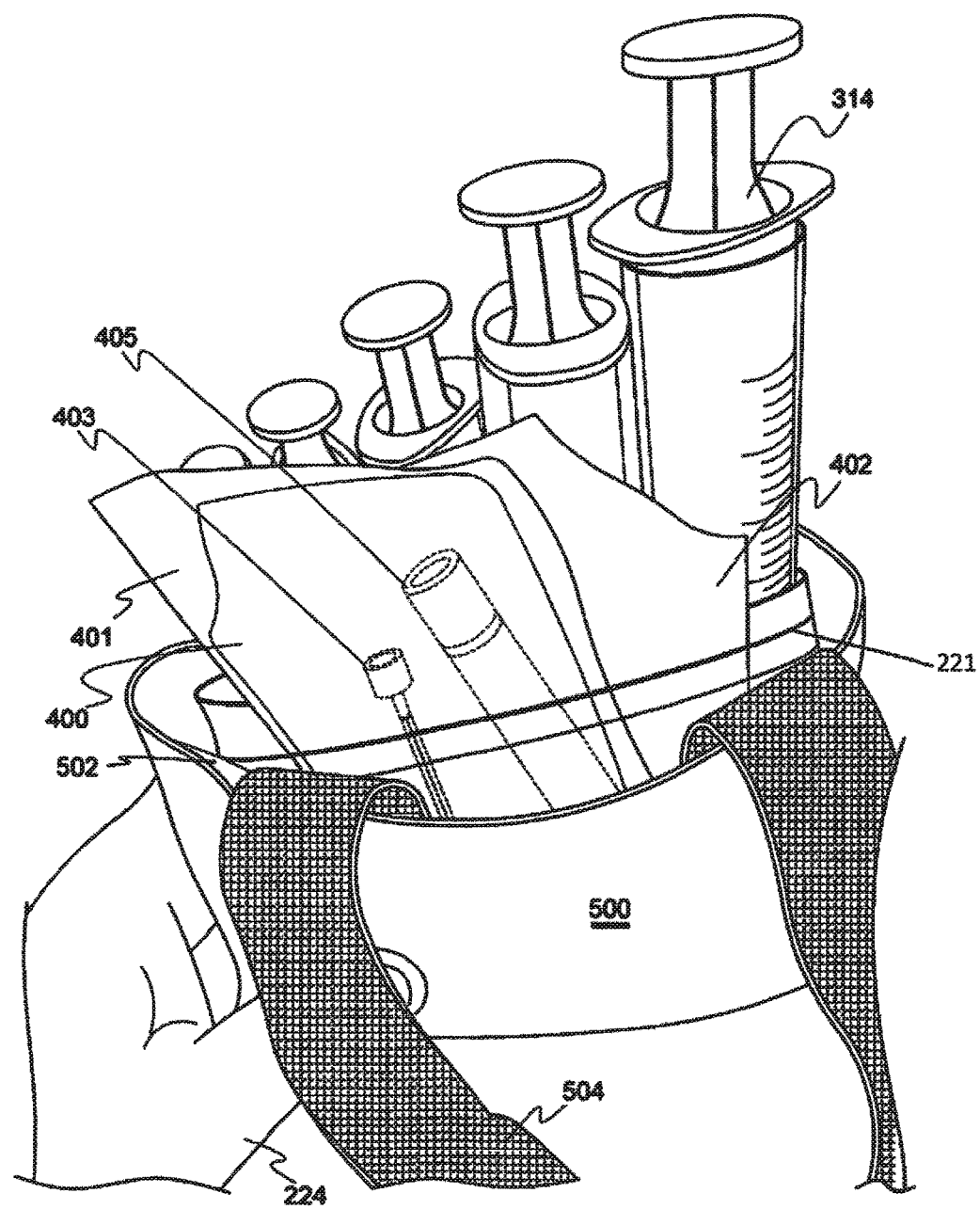
FIG. 14 is a side perspective view alternate of the view of the embodiment shown in FIG. 13.

Shown in FIGS. 13-14 are up to six single syringes 301-314 with nurse essentials 400, as described above and shown in FIGS. 8-12, and having an optional handbag 500 that can be preferably made of cloth. This can make ready use of the above pocket system. More particularly, the material of the handbag 500 may be made of plastic or non-plastic materials, may be soft, may be wipeable, and may be constructed of different colors, including clear and/or transparent colors. The system may be used with or without the strap 504 handbag 500, as required. The handbag is made or machine washable material.

Further shown in FIGS. 13 and 14 is a cover seal 502 to limit the extent that any syringes or minor nursing essentials shift or fall, from tipping or turning, out of any scrub pouches from the pouch itself.

The dimensions of the present handbag 500 have been configured for ergonomic effect on the wrist of a wearer, so that the handbag 500, does not extend above the highest syringe 314 of the system. The cloth used as a material for the handbag 500 may include a decorative branding or logo, or description, such as "Syringe Slots Holding System".

The foregoing has outlined the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

I claim:

1. A system for a plurality of syringes of different lengths and widths, the system comprising:
   a plurality of cylindrical tubes of at least two single rows of said cylindrical tubes, wherein each tube in said plurality of cylindrical tubes is configured to receive a syringe;
   a plurality of syringes corresponding to said plurality of cylindrical tubes;
   each tube in said plurality of cylindrical tubes having a different diameter than that of any other tube in said plurality of cylindrical tubes;
   each tube in said plurality of cylindrical tubes having a flat bottom surface, whereby each tube is provided stability from said flat bottom surface;
   a clear plastic vertical containment shroud for containing said cylindrical tubes and said plurality of syringes, wherein each tube in said plurality of cylindrical tubes rests vertically against other tubes in said plurality of cylindrical tubes, to contain said syringes within said system, and having a diameter encompassing the diameters of the tubes therein;
   said clear plastic vertical containment shroud configured to surround vertical sides of said plurality of cylindrical tubes to a partial height, wherein said partial height is configured to allow an upper portion of said plurality of cylindrical tubes to be exposed whereby a user may engage with said plurality of cylindrical tubes, and said vertical containment shroud structurally maintains a circumferential tight periphery around said vertical sides of said plurality of cylindrical tubes, whereby said containment shroud provides structural support for vertical positioning of said plurality of cylindrical tubes; and
   said vertical containment shroud providing a structural bottom surface, whereby said structural bottom surface of said vertical containment shroud does not obstruct the stability of said flat bottom surface of said plurality of cylindrical tubes.

2. The system as recited in claim 1, further comprising:
   at least a second row of said plurality of syringes and said plurality of tubes.

3. The system as recited in claim 2, further comprising a combination of a tube in said plurality of cylindrical tubes and a syringe in said plurality of syringes, wherein each tube-syringe combination is defined by diameters of 8 mm, 15 mm, 20 mm, 25 mm and 30 mm.

4. The system, as recited in claim 2, further comprising:
   a horizontal set of five groups of syringes and tubes.

5. The system as recited in claim 1, further comprising:
   each tube in said plurality of tubes having a horizontal lower surface thereof.

6. The system as recited in claim 1, in which said each cylindrical tube accommodates a needle with a volume in a range between 1 cc and a volume up to at least 30 cc.

7. The system as recited in claim 6, further comprising:
   a needle cap for each syringe in said plurality of syringes of the system.

8. The system as recited in claim 1, further comprising:
   a pouch affixed to a side of said vertical containment shroud; and
   minor nursing essentials contained in said pouch of said vertical containment shroud, wherein said minor nursing essentials include at least bandages, alcohol wipes, betadine, gauze, and tape.

9. The system as recited in claim 8, wherein said pouch further comprises:
   an upper end with an accessible slit for insertion of said minor nursing essentials.

10. The system as recited in claim 9, further comprising:
    a handbag of cloth adapted for an insertion of said vertical containment shroud with said pouch containing said minor nursing essentials, and said plurality of cylindrical tubes.

11. The system as recited in claim 10, further comprising:
    said handbag having handles extending above a highest tube in said plurality of cylindrical tubes.

12. The system as recited in claim 8, further comprising:
    a slightly weighted bottom surface of the system, to minimize tipping and lack of balance of the system.

13. A system for containing a plurality of syringes, the system comprising:
    a plurality of vertical tubes, wherein each tube in said plurality of vertical tubes is configured to receive a syringe;
    each tube in said plurality of vertical tubes having a flat bottom surface, whereby each tube is provided stability from said flat bottom surface;
    each tube in said plurality of vertical tubes having a concave rounded internal bottom surface, whereby said rounded surface is configured to guide a needle tip of a syringe toward a center of said rounded surface to thereby contain a syringe vertically;
    a vertical containment shroud configured to surround vertical sides of said plurality of vertical tubes to a partial height, wherein said partial height is configured to allow an upper portion of said plurality of vertical tubes to be exposed whereby a user may engage with said plurality of vertical tubes, and said vertical containment shroud structurally maintains a circumferential tight periphery around said vertical sides of said plurality of vertical tubes, whereby said containment shroud provides structural support for vertical positioning of said plurality of vertical tubes;
    said vertical containment shroud providing a structural bottom surface, whereby said structural bottom surface of said vertical containment shroud does not obstruct the stability of said flat bottom surface of said vertical tubes; and
    at least one tube in said plurality of vertical tubes is of a different diameter than at least one other tube in said plurality of vertical tubes.

14. The system as recited in claim 13, wherein said plurality of vertical tubes are fused together.

15. The system as recited in claim 13, wherein each tube in said plurality of vertical tubes differs in diameter from each other tube in said plurality of vertical tubes.

16. The system as recited in claim 13, wherein at least one tube in said plurality of vertical tubes is of a different height than at least one other tube in said plurality of vertical tubes.

17. The system as recited in claim 16, wherein each tube in said plurality of vertical tubes differs in height from each other tube in said plurality of vertical tubes.

18. The system as recited in claim 13, further comprising:
   a plurality of syringes, wherein each syringe in said plurality of syringes diametrically correlates to a diameter of a tube in said plurality of vertical tubes.

* * * * *